(12) United States Patent
Kane et al.

(10) Patent No.: US 11,191,641 B2
(45) Date of Patent: Dec. 7, 2021

(54) INDUCTANCE MODE DEPLOYMENT SENSORS FOR TRANSCATHETER VALVE SYSTEM

(71) Applicant: BOSTON SCIENTIFIC SCIMED, INC., Maple Grove, MN (US)

(72) Inventors: Michael J. Kane, Saint Paul, MN (US); Kevin Robert Poppe, New Brighton, MN (US); Stephen J. Burke, Clonmel (IE); Daniel J. Foster, Lino Lakes, MN (US); Peter James Keogh, Dublin (IE); Bradley S. Swehla, Eagan, MN (US); Christopher Jay Scheff, Elk River, MN (US); Laura Kathryn Irvine, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 216 days.

(21) Appl. No.: 16/252,959

(22) Filed: Jan. 21, 2019

(65) Prior Publication Data
US 2019/0224004 A1 Jul. 25, 2019

Related U.S. Application Data

(60) Provisional application No. 62/619,352, filed on Jan. 19, 2018.

(51) Int. Cl.
*A61F 2/24* (2006.01)
*A61F 2/966* (2013.01)
(Continued)

(52) U.S. Cl.
CPC ............ *A61F 2/243* (2013.01); *A61F 2/2439* (2013.01); *A61F 2/966* (2013.01); *A61M 25/005* (2013.01);
(Continued)

(58) Field of Classification Search
CPC . G01D 5/20; A61F 2/9517; A61F 2002/9511; A61F 2/2436;
(Continued)

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| AU | 2002329324 B2 | 7/2007 |
|---|---|---|
| CN | 1338951 A | 3/2002 |

(Continued)

OTHER PUBLICATIONS

US 8,062,356 B2, 11/2011, Salahieh et al. (withdrawn)
(Continued)

*Primary Examiner* — Katherine H Schwiker
*Assistant Examiner* — Andrew P. Restaino
(74) *Attorney, Agent, or Firm* — Seager, Tufte & Wickhem, LLP

(57) ABSTRACT

A delivery system for an implantable medical device includes an outer shaft defining an outer shaft lumen and an inner shaft translatable within the outer shaft lumen, the inner shaft defining a lumen extending through the inner shaft. An actuation mechanism extends through the lumen and includes a coupler, a force translation rod that extends proximally from the coupler and a plurality of push pull rods that extend distally from the coupler and that releasably couple to the implantable medical device. The force translation rod includes a transition in electromagnetic permeability. The delivery system includes an inductive coil disposed relative to the force translation rod and positioned (Continued)

to detect a change in inductance resulting from the transition in electromagnetic permeability passing through the inductive coil.

13 Claims, 14 Drawing Sheets

(51) Int. Cl.
*A61M 25/00* (2006.01)
*A61M 25/09* (2006.01)
*G01D 5/20* (2006.01)
*A61B 17/00* (2006.01)
*A61B 90/00* (2016.01)
*A61F 2/95* (2013.01)

(52) U.S. Cl.
CPC .............. *A61M 25/09* (2013.01); *G01D 5/20* (2013.01); *A61B 2017/00039* (2013.01); *A61B 2017/00292* (2013.01); *A61B 2017/00783* (2013.01); *A61B 2017/00876* (2013.01); *A61B 2017/00991* (2013.01); *A61B 2090/0811* (2016.02); *A61F 2/2436* (2013.01); *A61F 2/9517* (2020.05); *A61F 2002/9511* (2013.01); *A61F 2002/9665* (2013.01); *A61F 2210/0014* (2013.01); *A61F 2250/0096* (2013.01); *A61F 2250/0098* (2013.01); *A61M 25/0021* (2013.01); *A61M 2025/0004* (2013.01); *A61M 2025/09083* (2013.01)

(58) Field of Classification Search
CPC ...... A61F 2002/9665; A61F 2210/0014; A61F 2250/0096; A61F 2250/0098; A61F 2/243; A61F 2/966; A61F 2/2439; A61B 2017/00876; A61B 2017/00783; A61B 2090/0811; A61B 2017/00292; A61B 2017/00991; A61B 2017/00039; A61M 25/005; A61M 25/09; A61M 2025/0004; A61M 25/0021; A61M 2025/09083
See application file for complete search history.

(56) References Cited

U.S. PATENT DOCUMENTS

| | | |
|---|---|---|
| 2,701,559 A | 2/1955 | Cooper |
| 2,832,078 A | 4/1958 | Williams |
| 3,029,819 A | 4/1962 | Starks |
| 3,099,016 A | 7/1963 | Lowell |
| 3,113,586 A | 12/1963 | Edmark |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |

(56) References Cited

U.S. PATENT DOCUMENTS

| | | |
|---|---|---|
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |

(56) References Cited

U.S. PATENT DOCUMENTS

| | | | |
|---|---|---|---|
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B1 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,119 B1 * | 2/2004 | Di Caprio | A61M 25/0127 600/585 |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |

(56) References Cited

U.S. PATENT DOCUMENTS

| | | |
|---|---|---|
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,743 B2 | 4/2014 | Holecek et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |

(56) References Cited

U.S. PATENT DOCUMENTS

| | | |
|---|---|---|
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |

(56) References Cited

U.S. PATENT DOCUMENTS

| | | |
|---|---|---|
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0140006 A1* | 6/2008 | Eskuri .............. A61B 5/6848 604/117 |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0280495 A1 | 11/2010 | Paul et al. |
| 2010/0298931 A1 | 11/2010 | Quadri et al. |
| 2011/0257735 A1 | 10/2011 | Salahieh et al. |
| 2011/0264196 A1 | 10/2011 | Savage et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |

(56) References Cited

U.S. PATENT DOCUMENTS

| | | | |
|---|---|---|---|
| 2012/0089224 A1 | 4/2012 | Haug et al. | |
| 2012/0132547 A1 | 5/2012 | Salahieh et al. | |
| 2012/0172842 A1* | 7/2012 | Sela .................. | A61B 5/318 |
| | | | 604/528 |
| 2012/0179244 A1 | 7/2012 | Schankereli et al. | |
| 2012/0197379 A1 | 8/2012 | Laske et al. | |
| 2012/0303113 A1 | 11/2012 | Benichou et al. | |
| 2012/0303116 A1 | 11/2012 | Gorman et al. | |
| 2012/0330409 A1 | 12/2012 | Haug et al. | |
| 2013/0013057 A1 | 1/2013 | Salahieh et al. | |
| 2013/0018457 A1 | 1/2013 | Gregg et al. | |
| 2013/0030520 A1 | 1/2013 | Lee et al. | |
| 2013/0079867 A1 | 3/2013 | Hoffman et al. | |
| 2013/0079869 A1 | 3/2013 | Straubinger et al. | |
| 2013/0096664 A1 | 4/2013 | Goetz et al. | |
| 2013/0123796 A1 | 5/2013 | Sutton et al. | |
| 2013/0138207 A1 | 5/2013 | Quadri et al. | |
| 2013/0158656 A1 | 6/2013 | Sutton et al. | |
| 2013/0184813 A1 | 7/2013 | Quadri et al. | |
| 2013/0190865 A1 | 7/2013 | Anderson | |
| 2013/0304199 A1 | 11/2013 | Sutton et al. | |
| 2014/0018911 A1 | 1/2014 | Zhou et al. | |
| 2014/0094904 A1 | 4/2014 | Salahieh et al. | |
| 2014/0114405 A1 | 4/2014 | Paul et al. | |
| 2014/0114406 A1 | 4/2014 | Salahieh et al. | |
| 2014/0121766 A1 | 5/2014 | Salahieh et al. | |
| 2014/0135912 A1 | 5/2014 | Salahieh et al. | |
| 2014/0243967 A1 | 8/2014 | Salahieh et al. | |
| 2015/0012085 A1 | 1/2015 | Salahieh et al. | |
| 2015/0073540 A1 | 3/2015 | Salahieh et al. | |
| 2015/0073541 A1 | 3/2015 | Salahieh et al. | |
| 2015/0127094 A1 | 5/2015 | Salahieh et al. | |
| 2016/0045307 A1 | 2/2016 | Yohanan et al. | |
| 2016/0199184 A1 | 7/2016 | Ma et al. | |
| 2016/0367368 A1 | 12/2016 | Vidlund et al. | |
| 2017/0216029 A1 | 8/2017 | Crowley et al. | |
| 2018/0110965 A1* | 4/2018 | Gliner ................ | A61B 5/6851 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |

(56) References Cited

FOREIGN PATENT DOCUMENTS

| | | |
|---|---|---|
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2007035471 A2 | 3/2007 |
| WO | 2005102015 A3 | 4/2007 |
| WO | 2006138391 A2 | 4/2007 |
| WO | 2007044285 A2 | 4/2007 |
| WO | 2007058847 A2 | 5/2007 |
| WO | 2007092354 A2 | 8/2007 |
| WO | 2007097983 A1 | 8/2007 |
| WO | 2007053243 A2 | 9/2007 |
| WO | 2007033093 A2 | 1/2008 |
| WO | 2008073214 A2 | 6/2008 |
| WO | 200915486 A1 | 12/2009 |
| WO | 2010027485 A1 | 3/2010 |
| WO | 2010042950 A2 | 4/2010 |
| WO | 2010098857 A1 | 9/2010 |
| WO | 2012116368 A2 | 8/2012 |
| WO | 2012162228 A1 | 11/2012 |
| WO | 2013009975 A1 | 1/2013 |
| WO | 2013028387 A2 | 2/2013 |
| WO | 2013074671 A1 | 5/2013 |
| WO | 2013096545 A1 | 6/2013 |
| WO | 2014049477 A1 | 4/2014 |
| WO | 2016100806 A1 | 6/2016 |
| WO | 2016126511 A2 | 8/2016 |
| WO | 2017210085 A1 | 12/2017 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent-Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.

(56) References Cited

OTHER PUBLICATIONS

Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Knudsen et al., "Catheter-implanted prosthetic heart valves." Int'l J. of Art. Organs, 16(5): 253-262, May 1993.

Kort et al., "Minimally Invasive Aortic Valve Replacement: Echocardiographic and Clinical Results "Am. Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "Mycobacterium Chelonei Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48:S33-4(1989).
Maraj et al., Evaluation of Hemolysis in Patients with Prosthetic Heart Valves, Clin. Cardiol. 21, 387-392 (1998).
McKay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," ASAIO J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5 (6):491-9 (1991).
Pavcnik et al., "Percutaneous Bioprosthetic Venous Valve: A Long-term Study in Sheep." J. of Vascular Surg., 35(3): 698-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. 4/99.
Provisional U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al.,. "Stent Attachment Site-related Endoleakage after Stent Graft Treatment: An in vitro study of the effects of graft size, stent type, and atherosclerotic wall changes." J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).

(56) References Cited

OTHER PUBLICATIONS

Thompson et al., "Endoluminal stent grafting of the thoracic aorta: Initial experience with the Gore Excluder," Journal of Vascular Surgery, 1163-70 (Jun. 2002).
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).
Stassano, "Mid-term Results of the Valve on Valve Technique for Bioprosthetic failure." European journal of Ccardiothoracic Surgery:vol. 18, 453-457, Oct. 2000.
USPTO Case IPR 2017-0006, U.S. Pat. No. 8,992,608 B2, "Final Written Decision" dated Mar. 23, 2018.
Fluency Vascular Stent Graft Instructions for Use (2003).
International Search Report and Written Opinion dated Jul. 30, 2019 for International Application No. PCT/US2019/014406.
Carpentier-Edwards PERIMOUNT Bioprosthesis (2003).
Topol, "Percutaneous Expandable Prosthetic Valves." Textbook of Interventional Cardiology, W.B. Saunders Company, 2:1268-1276, 1994.
Vahanian et al., "Percutaneous Approaches to Valvular Disease." Circulation, 109:1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).

\* cited by examiner

INDUCTANCE MODE DEPLOYMENT SENSORS FOR TRANSCATHETER VALVE SYSTEM

CROSS-REFERENCE TO RELATED APPLICATIONS

This application claims the benefit of priority under 35 U.S.C. § 119 to U.S. Provisional Application Ser. No. 62/619,352, filed Jan. 19, 2018, the entirety of which is incorporated herein by reference.

TECHNICAL FIELD

The present disclosure pertains to medical devices, and methods for manufacturing medical devices. More particularly, the present disclosure pertains to medical delivery devices with position detection.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example of the disclosure is a delivery system for an implantable medical device. The delivery system includes an outer shaft defining an outer shaft lumen and an inner shaft that is translatable within the outer shaft lumen, the inner shaft defining a lumen extending through the inner shaft. An actuation mechanism extends through the lumen and includes a coupler, a force translation rod that extends proximally from the coupler and a plurality of push pull rods that extend distally from the coupler and that releasably couple to the implantable medical device. The force translation rod includes a transition in electromagnetic permeability. An inductive coil is disposed relative to the force translation rod and is positioned to detect a change in inductance resulting from the transition in electromagnetic permeability passing through the inductive coil.

Alternatively or additionally to any of the embodiments above, the transition in electromagnetic permeability may be positioned a distance from the coupler such that a detected change in inductance indicates a relative position of the coupler relative to the inductive coil.

Alternatively or additionally to any of the embodiments above, a portion of the force translation rod distal of the transition in electromagnetic permeability may be formed of a material having a first electromagnetic permeability and a portion of the force translation rod proximal of the transition in electromagnetic permeability may be formed of a material having a second electromagnetic permeability different from the first electromagnetic permeability.

Alternatively or additionally to any of the embodiments above, the force transition rod may be formed of a material having a low electromagnetic permeability material and the transition in electromagnetic permeability may include an inset band of a high electromagnetic permeability material.

Alternatively or additionally to any of the embodiments above, the force transition rod may include Nitinol as a low electromagnetic permeability material and stainless steel as a high electromagnetic permeability material.

Alternatively or additionally to any of the embodiments above, the inductive coil may have a constant windings pitch.

Alternatively or additionally to any of the embodiments above, the inductive coil may have a non-constant windings pitch in order to provide increased sensitivity to small movements of the transition in electromagnetic permeability relative to the inductive coil.

Alternatively or additionally to any of the embodiments above, the inductive coil may be disposed relative to the inner shaft.

Alternatively or additionally to any of the embodiments above, the inductive coil may be electrically coupled with a first coupling coil that is disposed relative to the inner shaft, at or near a proximal region of the delivery system, and may be magnetically coupled with a second coupling coil that is disposed about the outer shaft.

Another example of the disclosure is a delivery catheter for delivering an implantable medical device. The delivery catheter includes an outer shaft and an inner shaft that is slidingly disposed within the outer shaft and that defines a lumen extending through the inner shaft, with the implantable medical device securable relative to the inner shaft. A force translation rod extends through the lumen of the inner shaft and includes a first section formed of a material having a low electromagnetic permeability and a second section formed of a material having a high electromagnetic permeability such that a transition in electromagnetic permeability exists between the first section and the second section. An inductive coil is disposed relative to the force translation rod and is positioned to detect a change in inductance resulting from the transition in electromagnetic permeability passing through the inductive coil.

Alternatively or additionally to any of the embodiments above, the transition in electromagnetic permeability may be positioned a known distance from where the implantable medical device is secured relative to the inner shaft.

Alternatively or additionally to any of the embodiments above, the force translation rod may extend distally to a coupler, and a plurality of push pull rods may extend distally from the coupler, and the transition in electromagnetic permeability may be positioned a known distance from the coupler.

Alternatively or additionally to any of the embodiments above, the inductive coil may have a constant windings pitch.

Alternatively or additionally to any of the embodiments above, the inductive coil may be disposed relative to the inner shaft.

Alternatively or additionally to any of the embodiments above, the inductive coil may be electrically coupled with a first coupling coil that is disposed relative to the inner shaft, at or near a proximal region of the delivery catheter, and may be magnetically coupled with a second coupling coil that is disposed about the outer shaft.

Another example of the disclosure is a delivery system for an implantable medical device. The delivery system includes a shaft defining a lumen and an actuation mechanism that extends through the lumen. The actuation member includes a coupler, a force translation rod that extends proximally from the coupler and a plurality of push pull rods that extend distally from the coupler and that releasably couple to the implantable medical device. The force translation rod includes a transition in electromagnetic permeability. An inductive coil is disposed relative to the force translation rod and is positioned to detect a change in inductance resulting from the transition in electromagnetic permeability passing through the inductive coil.

Alternatively or additionally to any of the embodiments above, the transition in electromagnetic permeability may be positioned a distance from the coupler such that a detected change in inductance indicates a relative position of the coupler relative to the inductive coil.

Alternatively or additionally to any of the embodiments above, a portion of the force translation rod distal of the transition in electromagnetic permeability may be formed of a material having a first electromagnetic permeability and a portion of the force translation rod proximal of the transition in electromagnetic permeability may be formed of a material having an electromagnetic permeability different from the first electromagnetic permeability.

Alternatively or additionally to any of the embodiments above, the force transition rod may be formed of a material having a low electromagnetic permeability material and the transition in electromagnetic permeability may include an inset band of a high electromagnetic permeability material.

Alternatively or additionally to any of the embodiments above, the inductive coil may be electrically coupled with a first coupling coil that is disposed relative to the inner shaft, at or near a proximal region of the delivery system, and may be magnetically coupled with a second coupling coil that is disposed about the outer shaft.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
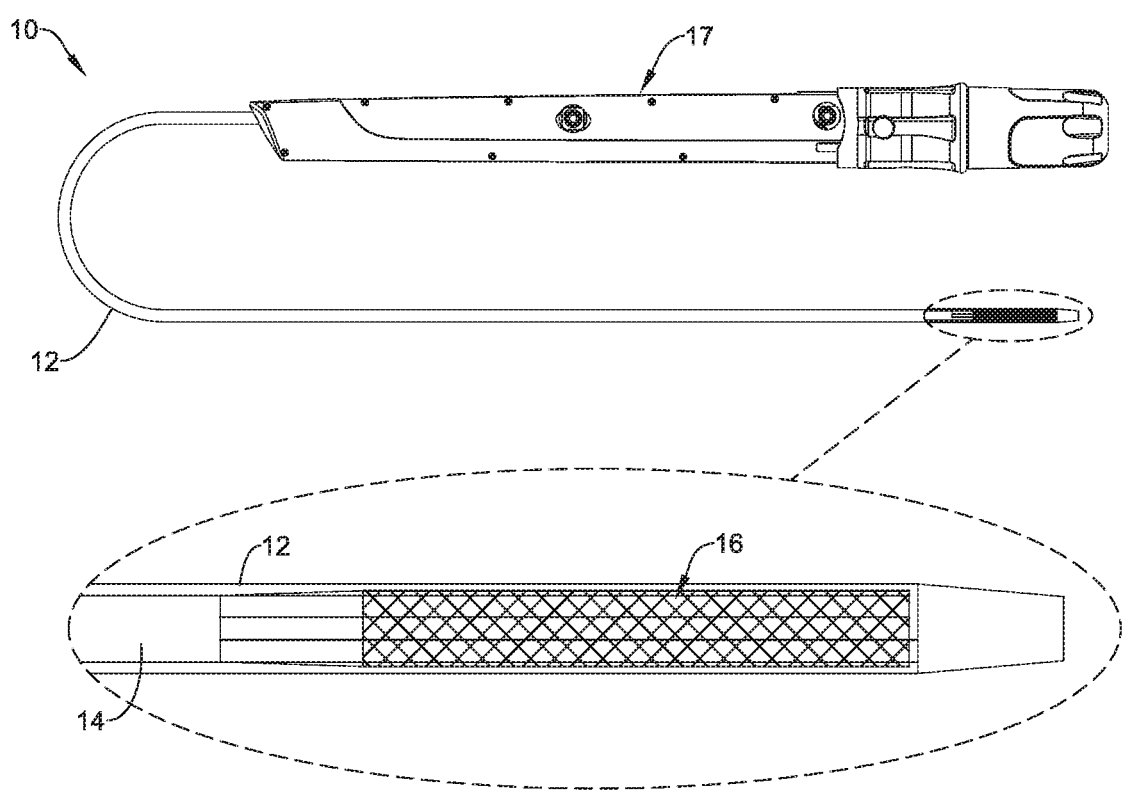
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, a tubular member (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. For example, in some instances the inner catheter (or components thereof) may be coupled to medical implant 16 whereby actuation of the inner catheter 14 relative to the outer sheath 12 and/or the medical implant 16 may deploy the medical device 16 within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system 10 may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
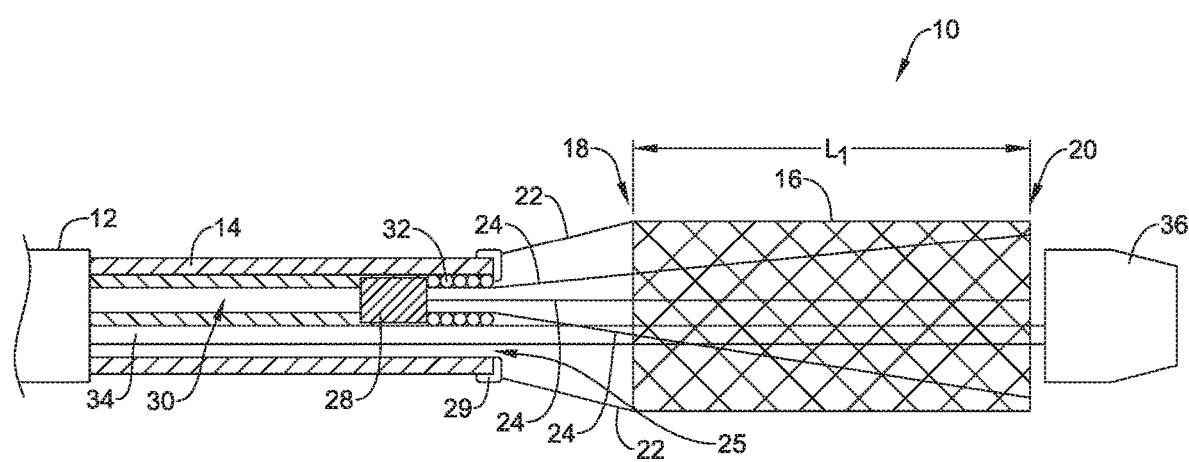
FIG. 2 is a partial cross-sectional view of a portion of an example medical device delivery system.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially deployed position after the outer sheath has been retracted to uncover the implant 16. For example, FIG. 2 illustrates that the support members 22 may be designed such that the distal end of each of the support members may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 28 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to- proximal direction such that the translation of the translation members (via operator manipulation at the handle, for example) may "pull" the distal end 20 of the implant closer to the proximal end 18 of the implant 16.

Figure 3:
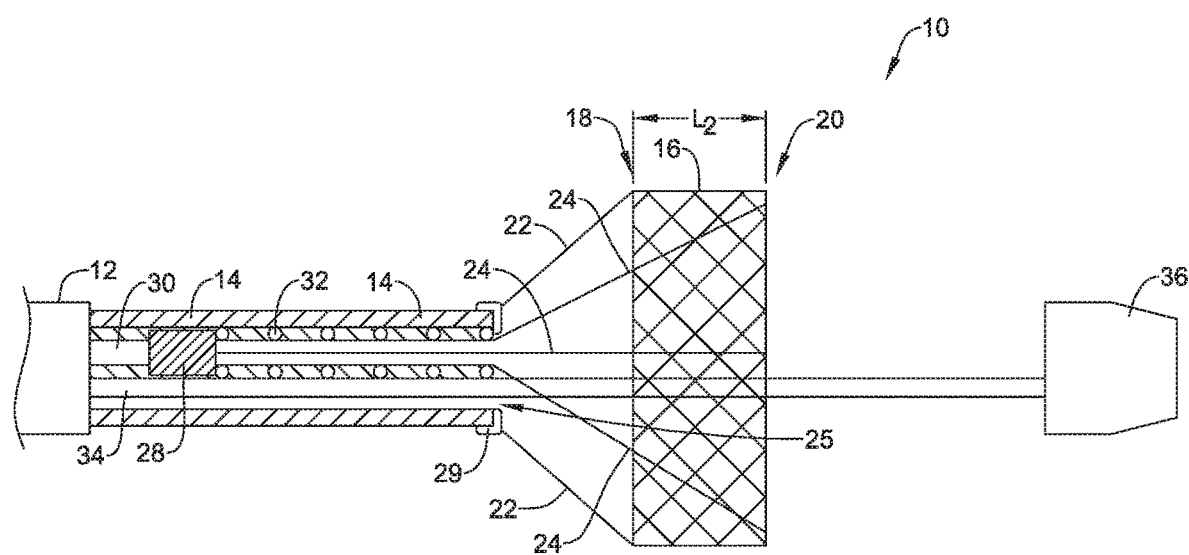
FIG. 3 is a partial cross-sectional view of a portion of an example medical device delivery system.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as $L_2$, whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16.

In some examples, an operator may be able to manipulate the translation members 24 via the handle member 17. For example, the handle 17 may include an actuation member designed to control the translation of the translation members 24. FIG. 2 illustrates that the handle member 17 may be coupled to the translation members 24 via an actuation shaft 30 and a coupling member 28. For example, as will be described in greater detail below, FIG. 2 illustrates that the proximal ends of the translation members 24 may be coupled to a distal end of the coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner shaft 14 from the coupling member 28 to the handle member 17.

For purposes of discussion herein, the inner shaft 14 may also be referred to as an inner member or liner 14. The liner 14 may include a number of different features shown in the figures described herein. For example, the liner may include a lumen 25. Further, the translation members 24, coupler 28, actuation shaft 30, guidewire lumen 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may be designed to permit a guidewire to extend and translate therein. Further, the tubular guidewire member 34 may extend from the handle member 17, through the lumen 25 of the inner member 14, through the implant 16 and terminate at a nosecone 36. Additionally the tubular guidewire member 34 may include a lumen (not shown in FIG. 2 or FIG. 3) that permits a guidewire to be advanced therein. In other words, the medical device 10 may be advanced to a target site within a body over a guidewire extending within the lumen of the tubular guidewire member 34.

Figure 4:
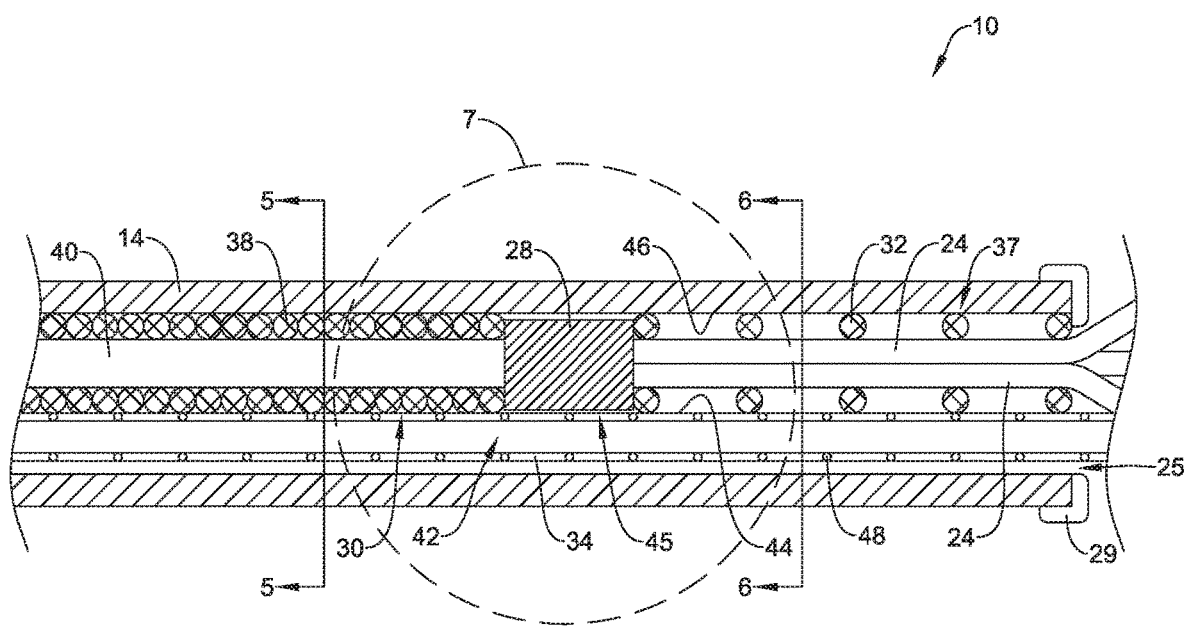
FIG. 4 is a partial cross-sectional view of a portion of the catheter shaft shown in FIGS. 1-3.

FIG. 4 illustrates a cross-section of a portion of the medical device system 10 described with respect to FIGS.

1-3. In particular, as described above, FIG. 4 illustrates the actuation shaft 30 coupled to coupler 28, translation members 24 coupled to coupler 28 and grouping coil 32 (the distal end of which is positioned adjacent the containment fitting 29, as described above) wound around the translation members 24. FIG. 4 further illustrates that the outer surface 37 of the grouping coil 32 may contact both the inner surface 46 of the inner catheter 14 and the outer surface 44 of the guidewire member 34. Therefore, it can be further appreciated that the outer diameter (and therefore the inner diameter) of the grouping coil 32 may remain constant as the grouping coil lengthens or shortens as the coupler 28 translates within the lumen 25 of the inner catheter 14.

Additionally, it can be appreciated that the medical device system 10 may be designed such that both the proximal end and the distal end of the grouping coil 32 may not be fixedly attached to adjacent structures (e.g., may not be attached to the coupling member 28 and/or the containment fitting 29). It can be appreciated that by not attaching either end of the grouping coil 32 to any adjacent structures (e.g., the coupling member 28 and/or the containment fitting 29), the grouping coil 32 is permitted to twist freely while lengthening or shortening within the lumen 25. This freedom of movement allows the grouping coil 32 to maintain an inner diameter which tightly groups (e.g., contains) the translation members 24 to each other as that translate linearly within the lumen 25 of inner catheter 14.

FIG. 4 further illustrates that coupler 28 may be positioned within the lumen 25 of the inner catheter 14 such that the bottom surface 45 of the coupler 28 is adjacent to the outer surface 44 of the guidewire member 34. In some examples, the coupler 28 may be designed such that it is not rigidly fixed to the guidewire member 34, and therefore, may translate relative to the guidewire member 34. In other examples, the coupler 28 may be designed such that it is rigidly fixed to the guidewire member 34, and therefore, translation of coupler 28 (which itself may occur via translation of the actuation shaft 30) may also translate both the guidewire member 34 and the translation members 24. In other words, it can be appreciated that in instances where the coupler 28 is rigidly fixed to the guidewire member 34, an operator manipulating the actuation shaft 30 via handle 17 may translate both the translation members 24 and the guidewire member 34 together such that distal or proximal translation of either the translation members 24 or the guidewire member 34 will translate both the translation members 24 or the guidewire member 34 a correspondingly equal amount. Further, it can be appreciated the same effect may be achieved by coupling the guidewire member 34 and the actuation shaft 30 anywhere along medical device system 10, including coupling the guidewire member 34 and the actuation shaft 30 to one another in the handle member 17. It can be appreciated that the guidewire member 34 and the actuation shaft 30 may be coupled together in more than one location along medical device system 10.

In some instances, it may be desirable for the nosecone 36 to translate in a proximal direction as the implantable medical device 16 shifts from a collapsed configuration to a fully deployed configuration (as shown in FIGS. 1-3). It can be appreciated from the above discussion that because the nosecone 36 is connected to the distal end of the guidewire member 34, that as the guidewire member 34 translates with the translation members 24 (via the coupler 28 and actuation shaft 30), the nosecone 36 with correspondingly translate in a proximal direction as the translational members act to shift the implantable medical device 16 from a collapsed to a fully deployed configuration.

FIG. 4 further illustrates that in some instances actuation shaft 30 may include an actuation rod 40 positioned within the lumen of a coil member 38. Similar to that described above with respect to the grouping coil 32, the outer surface of the coil member 38 may contact both the inner surface 46 of the inner catheter 14 and the outer surface 44 of the guidewire member 34. It can be appreciated that the outer surface of the coil member 38 may reduce the frictional forces of actuation shaft 30 along the inner surface 46 of the inner catheter 14 as compared to the frictional forces that would be present if the actuation shaft 30 did not include a coil member. For example, coil member 38 provides both "point to point" contacts along the inner surface 46 of the inner member 14 in addition to increasing the ease with which the actuation shaft flexes/bends within the lumen 25 of inner catheter 14. These properties reduce the overall surface friction between the outer surface of actuation shaft 30 and the inner surface 46 of inner catheter 14 (as compared to a solid rod of similar proportions). The reduction in friction may further reduce the likelihood of the actuation shaft 30 to store and release energy in the form of a "backlash" effect. It is contemplated that the coil member 38 may be extend along a portion of or the entire length of the actuation rod 40. Further, the actuation rod 40 may extend from the proximal end of the coupler 28 to the handle member 17. Additionally, the above described functional characteristics of the coil member 38 are not intended to be limiting. For example, it is contemplated that the coil member 38 may be utilized to conduct electricity along a portion thereof (e.g., along the surface or other portion of coil member 38).

FIG. 4 further illustrates that in some examples guidewire member 34 may include a reinforcing coil embedded with its tubular wall. For example, FIG. 4 shows coil 48 positioned with the wall of guidewire member 34. Coil 48 may provide additional strength and flexibility to the guidewire member 34. Additionally, FIG. 4 illustrates the lumen 42 of the guidewire member 34. It can be appreciated that a guidewire (not shown) may extend with the lumen 42 of the guidewire member 34.

Figure 5:
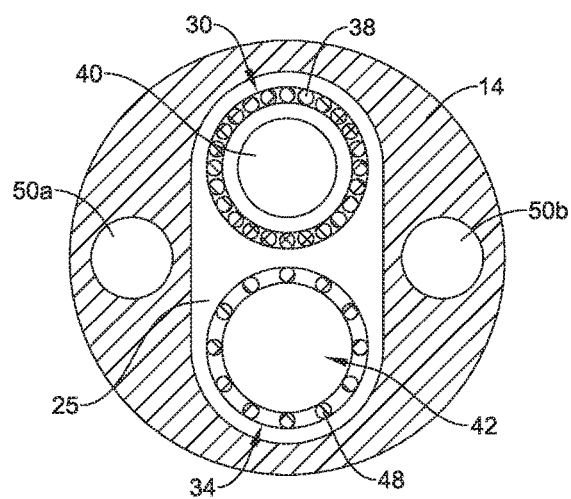
FIG. 5 is a cross-sectional view along line 5-5 of FIG. 4.

FIG. 5 illustrates a cross-sectional view along line 5-5 of FIG. 4. As indicated above, the inner catheter 14 may include a number of features. For example, the inner catheter 14 may include one or more tension resistance members 50a/50b. The tension resistance members 50a/50b may take the form of a wire (e.g., a metallic wire), a braid, cable, stranded cable, a composite structure, or the like. In one example, the tension resistance members 50a/50b are both metallic wires. In another instance, the tension resistance members 50a/50b are both metallic braids. The braids may further include an axial wire made from a suitable polymer or metal (e.g., aramid). The tension resistance members 50a/50b may be made from the same materials and/or have the same configuration. Alternatively, the tension resistance members 50a/50b may be different from one another. Furthermore, while FIG. 2 illustrates that the inner catheter 14 includes two tension resistance members 50a/50b, this is not intended to be limiting. Other numbers of tension resistance members 50a/50b are contemplated such as one, three, four, five, six, seven, or more.

FIG. 5 further illustrates that the shape of the lumen 25 of the inner catheter 14 may be designed to limit twisting of the actuation shaft 30 and the guidewire member 34. For example, FIG. 5 illustrates that lumen 25 may be non-circular. For example, the shape of the lumen 25 may be ovular, square, rectangular, etc. It can be appreciated that as the inner catheter 14 rotates within the lumen of the outer member 12, the shape of the lumen 25 may force both the actuation shaft 30 and the guidewire member 34 to maintain the respective spatial relationship as depicted in FIG. 5. In other words, the shape of the lumen 25 forces the actuation shaft 30 and the guidewire member 34 to remain in their positions relative to one another independent of the bending, rotating, flexing, etc. of the inner catheter 14.

Additionally, FIG. 5 also illustrates the actuation shaft 30 and the guidewire member positioned adjacent one another within lumen 25. As described above, actuation shaft 30 may include an actuation rod 40 positioned within the lumen of a coil member 38. Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

Figure 6:
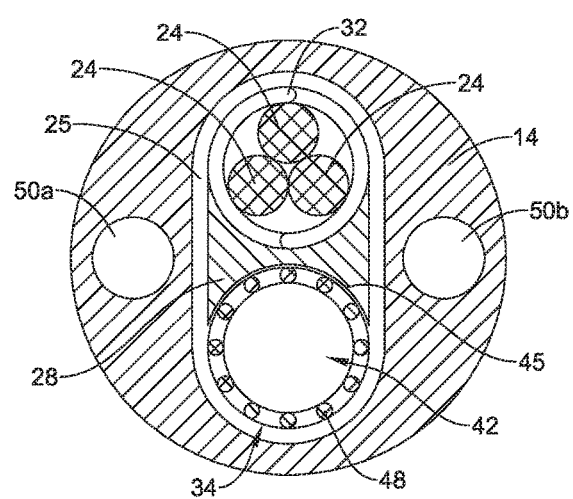
FIG. 6 is a cross-sectional view along line 6-6 of FIG. 4.

FIG. 6 illustrates a cross-sectional view along line 6-6 of FIG. 4. FIG. 4 shows grouping coil 32, coupler 28 and guidewire member 34 positioned within lumen 25. Additionally, FIG. 6 shows that the grouping coil 32 may surround three translational members 24 positioned therein. The translational members 24 may be spaced equidistance from one another. For example, the translational members 24 may be spaced at substantially 120 degree angles relative to one another. Further, while FIG. 6 shows three translational members 24, it is contemplated that more or less than three translational members 24 may be utilized within medical device system 10. For example, medical device system 10 may include 1, 2, 3, 4, 5, 6, 7, 8, 9, 10 or more translational members 24.

Additionally, FIG. 6 illustrates that inner catheter 14 may include one or more tension resistance members 50a/50b. The tension resistance members 50a/50b may take the form of a wire (e.g., a metallic wire), a braid, cable, stranded cable, a composite structure, or the like. Further, FIG. 6 illustrates that tension resistance members 50a/50b may be positioned opposite one another on either side of lumen 25.

Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

FIG. 6 further illustrates the coupler 28 including the bottom surface 45 (described above). As illustrated, the bottom surface 45 is shaped to mate with the outer surface the guidewire member 34. For example, in some examples, the bottom surface 45 may include a curved portion which mates with the radius defined by the outer surface 44 of the guidewire member 34. As described above, the bottom surface 45 of the coupler 28 may or may not be rigidly fixed to the guidewire member 34.

Figure 7:
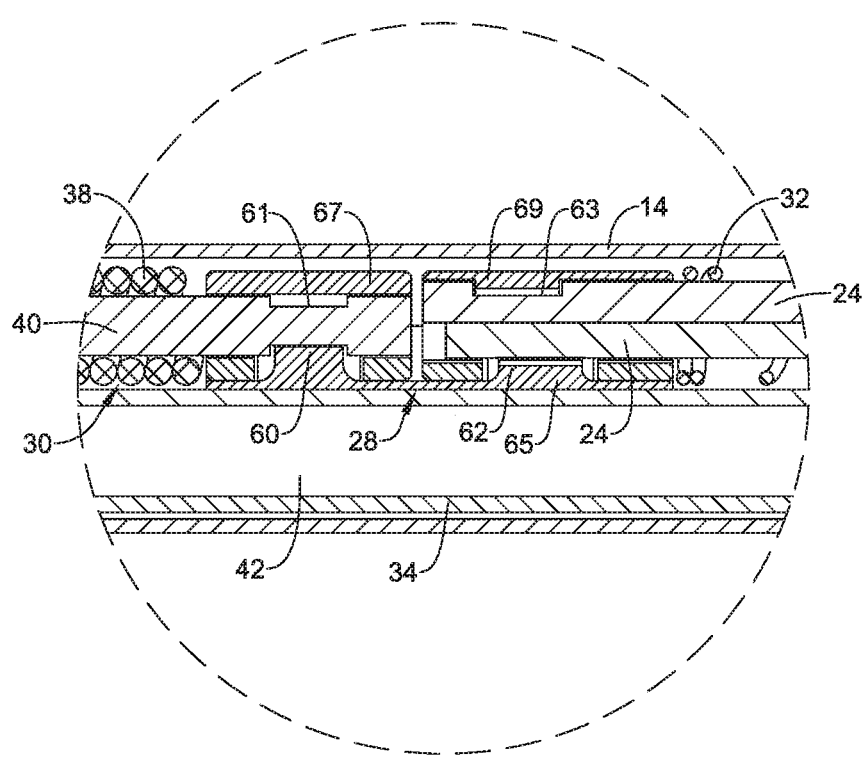
FIG. 7 is a partial cross-sectional view of a portion of an example medical device delivery system.

FIG. 7 illustrates a detailed view of a portion of the medical device system 10 shown in FIG. 6. Further, FIG. 7 illustrates a cross-sectional view of coupler 28. Coupler 28 may include a base member 65, a first cap 67 and a second cap 69. First cap 67 and second cap 69 may be separate components from base member 65. Further, first cap 67 and second cap 69 may be attached to base member 65 via welding or any other suitable process.

As shown, a portion of the actuation rod 40 may extend into a portion of coupler 28 and thereby contact both base member 65 and first cap 67. Similarly, portions of the translational members 24 may extend into a portion of coupler 28 and thereby contact both base member 65 and first cap 69. It can be appreciated from FIG. 7 that base member 65 may include one or more projections 60 that mate with one or more recess 61 in the actuation rod 40. Similarly, it can be appreciated from FIG. 7 that base member 65 may include one or more projections 62 that mate with one or more recesses 63 in the translational members 24. It can further be appreciated that engaging a respective projection with a recess portion (in both the actuation rod 40 and the translational members 24) may limit translational movement of both the actuation rod 40 and the translational members 24 relative to the coupler. In other words, engagement of a respective projection with a recess portion (in both the actuation rod 40 and the translational members 24) may prevent both the actuation rod 40 and the translational members 24 from translating independently of the coupler 28 (and one another). However, it can be further appreciated that the engagement of a respective projection with a recess portion (in both the actuation rod 40 and the translational members 24) may permit the actuation rod 40 to spin/swivel on its own longitudinal axis. Additionally, it can be appreciated that coupler 28 (including base member 65, first cap 67 and second cap 69) may permit dissimilar materials to be engaged because they are mechanically "trapped" and preferentially oriented within coupler 28. In some instances, the coupler 28 may be defined as a "swivel."

Figure 8A:
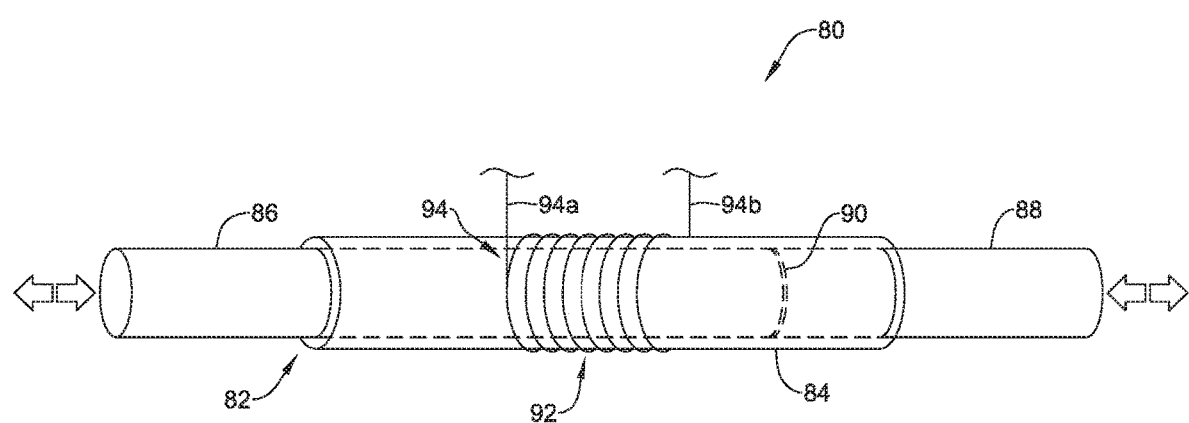
FIG. 8A through FIG. 8C are side views of a portion of an example medical device delivery system.
Figure 8B:
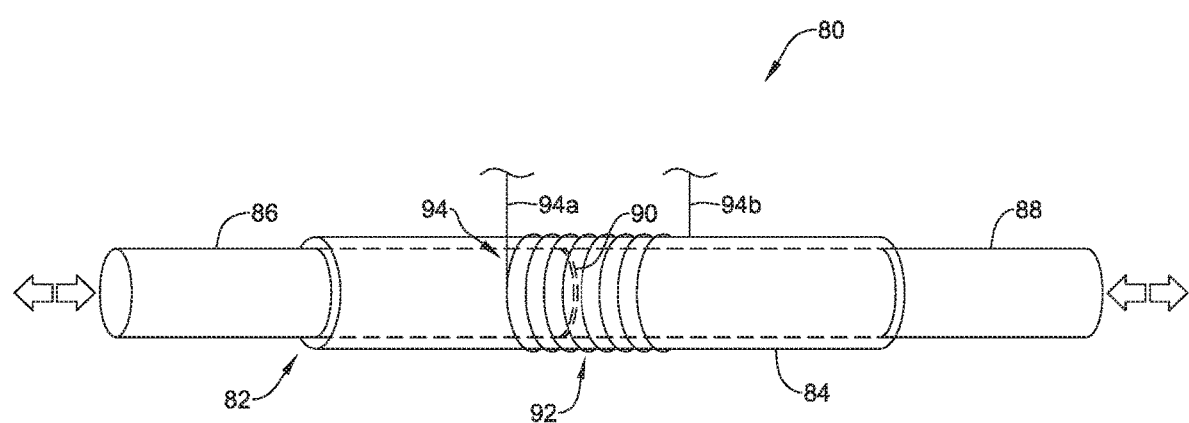
Figure 8C:
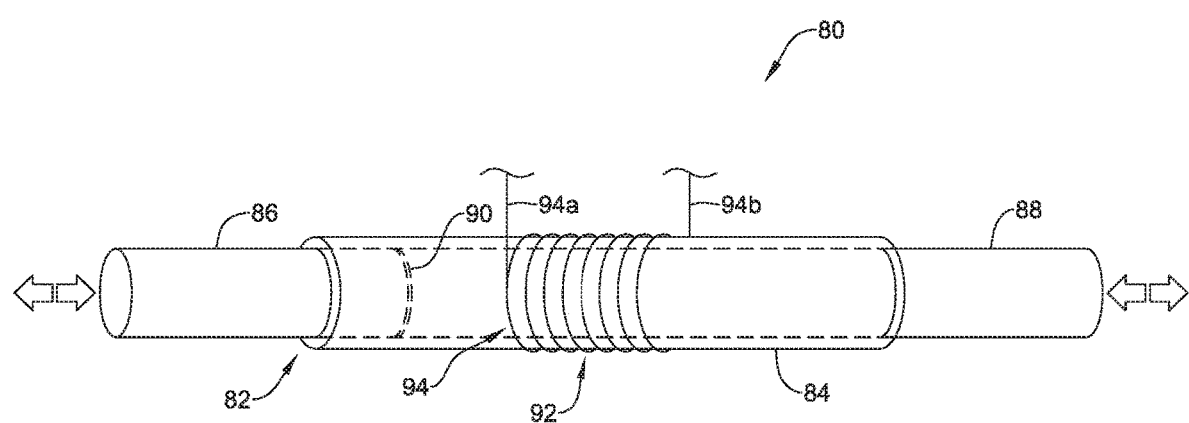

In some cases, it can be beneficial to have an indication of relative position of the actuation rod 40, and thus an indication of the relative position of the coupler 28 and the translational members 24, as this can provide an indication of the relative position of the medical implant 16. FIGS. 8A-8C show a portion of an example medical delivery device 80. It will be appreciated that some features and elements of the medical delivery device 80 may not be illustrated for clarity purposes. The medical delivery device 80 includes an inner rod 82 that is slidingly disposed within an outer sheath 84. In some cases, the inner rod 82 may be considered as representing the actuation rod 40 and the outer sheath 84 may be considered as representing a portion of the inner catheter 14 discussed with respect to previous drawings. In some cases, the outer sheath 84 includes an electrically insulating layer. In some instances, the outer sheath 84 may represent or be a portion of the coil member 38 extending through the lumen 25.

In some cases, as illustrated, the inner rod 82 may include a first section 86 that is formed of a material having a first electromagnetic permeability, a second section 88 that is formed of a material having a second electromagnetic permeability that is different from the first electromagnetic permeability, and an intervening transition in electromagnetic permeability 90. While the first section 86 is labeled as being formed of a material with low electromagnetic permeability and the second section 88 is labeled as being formed of a material with high electromagnetic permeability, this is just an example. In some cases, the low electromagnetic permeability material and the high electromagnetic permeability material may be reversed from what is shown, for example. In some instances, the relative length of the first section 86 and the second section 88 may vary. In some cases, the first section 86 may have a longer or even substantially longer length than the second section 88. In some cases, the second section 88 may have a longer length than the first section 86. These are just examples.

The medical delivery device 80 includes an inductive coil 92 that is disposed relative to the outer sheath 84. The inductive coil 92 is formed of a wire 94 that forms a number of windings around the outer sheath 84. The wire 94 has free ends 94a, 94b that extend proximally to the handle 17 as shown in FIG. 1 so that an electrical signal inductively generated in the inductive coil 92 and carried by the wire 94 may be sent to a measurement circuit, for example. As the inner rod 82 moves distally relative to the outer sheath 84, the transition in electromagnetic permeability 90 will create a change in the induced current caused by the inner rod 82 moving through the inductive coil 92. As seen in FIG. 8A, the transition in electromagnetic permeability 90 is proximal of the inductive coil 92. In FIG. 8B, the transition in electromagnetic permeability 90 is disposed within the inductive coil 92. In FIG. 8C, the transition in electromagnetic permeability 90 has passed completely through the inductive coil 92 and is now distal of the inductive coil 92.

Figure 8D:
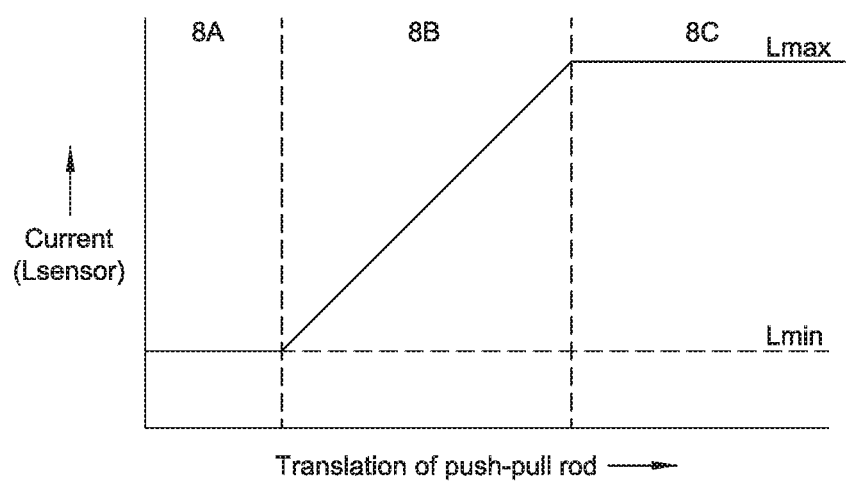
FIG. 8D is a graphical representation of operation of the example medical device delivery system of FIG. 8A through FIG. 8C.

FIG. 8D is a graphical representation of how changes in electromagnetic permeability can be seen, assuming that the first section 86 is formed (as labeled) of a low electromagnetic permeability material and the second section 88 is formed of a high electromagnetic permeability material. When the transition in electromagnetic permeability 90 remains proximal of the inductive coil 92, as shown in FIG. 8A, the induced current is relatively low. This is labeled as region 8A in FIG. 8D. When the transition in electromagnetic permeability 90 is passing through the inductive coil 92, as shown in FIG. 8B, the induced current increases. This is labeled as region 8B in FIG. 8D. Once the transition in electromagnetic permeability 90 has passed completely through the inductive coil 92, and hence only the second section 88 (formed of a high electromagnetic permeability material) is within the inductive coil 92, the induced current is at a maximum. This is labeled as region 8C in FIG. 8D. In some cases, the material with a low electromagnetic permeability may be a nickel-titanium alloy such as Nitinol, and the material with a high electromagnetic permeability may be a stainless steel, but this is merely an example. Some stainless steels are relatively low in electromagnetic permeability.

In some cases, as described, a change in inductance may be detected. In some instances, there are other electromagnetic properties that are related to inductance that may also be detected and/or measured. Magnetic reluctance is an example of such a property. Examples of circuit-related properties include resonant frequency, Q factor, impulse response, decay time, phase shift, amplitude response, spectral filtering response, impedance, reactance, admittance, suceptance, step response and combinations thereof.

Figure 9A:
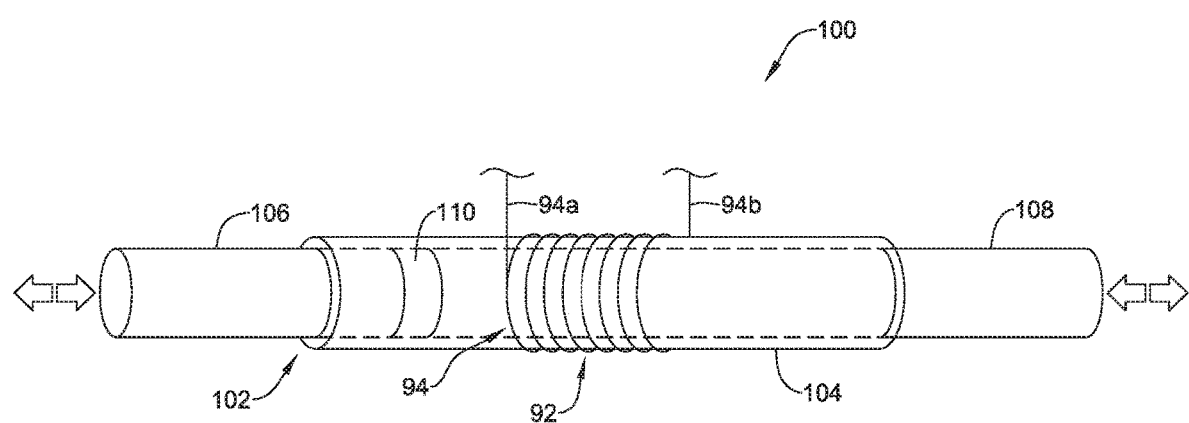
FIG. 9A is a side view views of a portion of an example medical device delivery system.

FIG. 9A shows a portion of an example medical delivery device 100. It will be appreciated that some features and elements of the medical delivery device 100 may not be illustrated for clarity purposes. The medical delivery device 100 includes an inner rod 102 that is slidingly disposed within an outer sheath 104. In some cases, the inner rod 102 may be considered as representing the actuation rod 40 and the outer sheath 104 may be considered as representing a portion of the inner catheter 14 discussed with respect to previous drawings. In some cases, the outer sheath 104 includes an electrically insulating layer. In some instances, the outer sheath 104 may represent or be a portion of the coil member 38 extending through the lumen 25. The medical delivery device 100 includes an inductive coil 92 that is disposed relative to the outer sheath 84. The inductive coil 92 is formed of a wire 94 that forms a number of windings around the outer sheath 84. The wire 94 has free ends 94a, 94b that extend proximally to the handle 17 as shown in FIG. 1 so that an electrical signal inductively generated in the inductive coil 92 and carried by the wire 94 may be sent to a measurement circuit, for example.

Figure 9B:
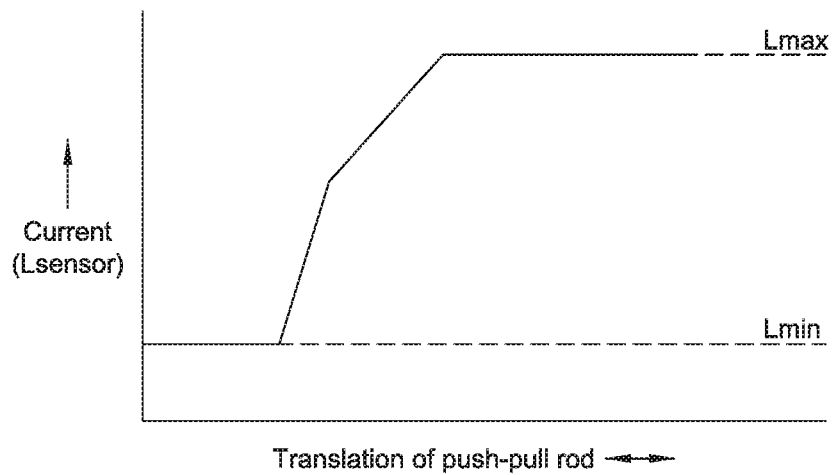
FIG. 9B is a graphical representation of operation of the example medical device delivery system of FIG. 9A.

In some cases, as illustrated, the inner rod 102 may be formed of a material having a particular electromagnetic permeability. In some instances, the inner rod 102 may include a first section 106 formed of a first material and a second section 108 that is formed of a different material. The first section 106 may have a lower or higher electromagnetic permeability than the second section 108. In some cases, the first section 106 and the second section 108 may be formed of the same material, and thus may have the same electromagnetic permeability. In some cases, the inner rod 102 may include an inset ring 110 that is formed of a material having a very high electromagnetic permeability. The inset ring 110 may, for example, be formed of ferrite or mu- metal. As the inner rod 102 translates relative to the outer sheath 104, and the inset ring 110 passes through the inductive coil 92, it will be appreciated that, relative to what was shown in FIG. 8D, there will be a steeper transition in the induced coil, as can be seen for example in FIG. 9B, which is a graphical representation.

Figure 10:
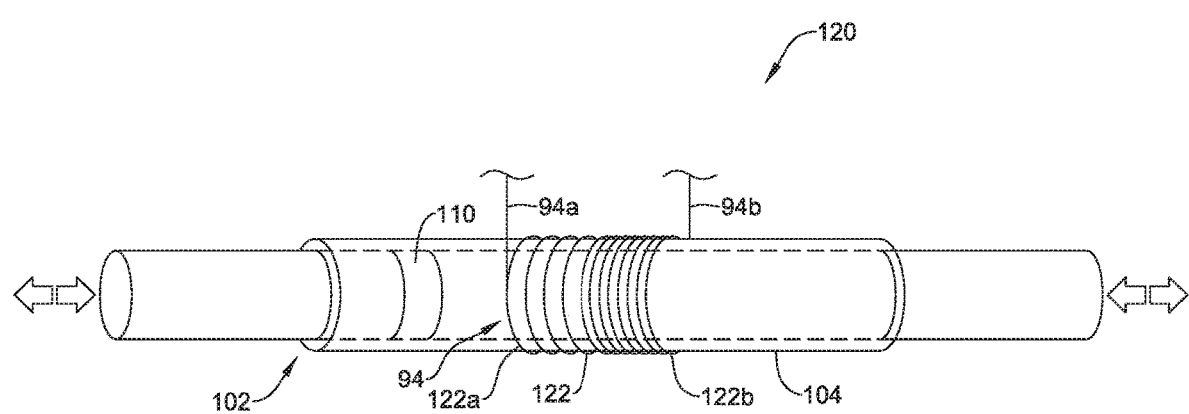
FIG. 10 is a side view of a portion of an example medical device delivery system.

FIG. 10 shows a portion of an example medical delivery device 120. It will be appreciated that some features and elements of the medical delivery device 120 may not be illustrated for clarity purposes. The medical delivery device 120 includes an inner rod 102 that is slidingly disposed within an outer sheath 104. In some cases, the inner rod 102 may be considered as representing the actuation rod 40 and the outer sheath 104 may be considered as representing a portion of the inner catheter 14 discussed with respect to previous drawings. In some cases, the outer sheath 104 includes an electrically insulating layer. In some instances, the outer sheath 104 may represent or be a portion of the coil member 38 extending through the lumen 25. The medical delivery device 120 includes an inductive coil 122 that is disposed relative to the outer sheath 104. The inductive coil 122 is formed of a wire 94 that forms a number of windings around the outer sheath 84 and includes free ends 94a, 94b that can extend proximally to the handle 17. In some cases, as shown, the inductive coil 122 has a variable windings pitch, varying from a relatively wider pitch at a distal end 122a of the inductive coil 122 to a relatively narrower pitch at a proximal end 122b of the inductive coil 122. In some cases, having a variable pitch enables an extended range and extended precision while also enabling improved signal to noise (S/N) values.

Figure 11:
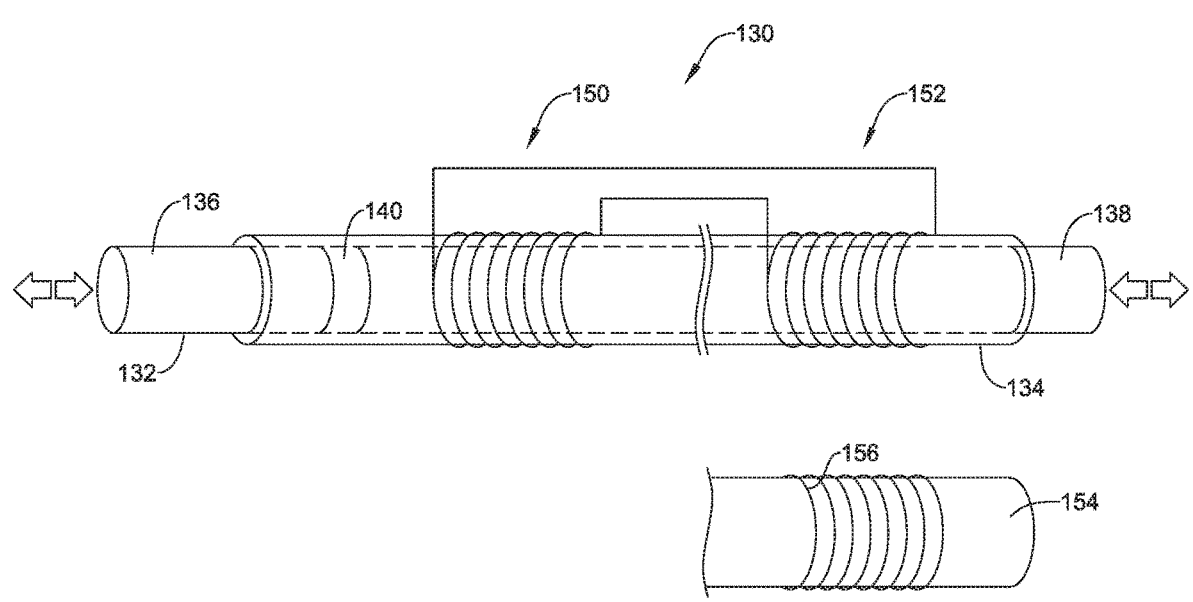
FIG. 11 is a side view of a portion of an example medical device delivery system.

FIG. 11 shows a portion of an example medical delivery device 130. It will be appreciated that some features and elements of the medical delivery device 130 may not be illustrated for clarity purposes. The medical delivery device 130 includes an inner rod 132 that is slidingly disposed within an outer sheath 134. In some cases, the inner rod 132 may be considered as representing the actuation rod 40 and the outer sheath 134 may be considered as representing a portion of the inner catheter 14 discussed with respect to previous drawings. In some cases, the outer sheath 134 includes an electrically insulating layer. In some instances, the outer sheath 134 may represent or be a portion of the coil member 38 extending through the lumen 25.

In some cases, as illustrated, the inner rod 132 may be formed of a material having a particular electromagnetic permeability. In some instances, the inner rod 132 may include a first section 136 formed of a first material and a second section 138 that is formed of a different material. The first section 136 may have a lower or higher electromagnetic permeability than the second section 138. In some cases, the first section 136 and the second section 138 may be formed of the same material, and thus may have the same electromagnetic permeability. In some cases, the inner rod 132 may include an inset ring 140 that is formed of a material having a very high electromagnetic permeability. The inset ring 140 may, for example, be formed of ferrite or mu- metal.

In some instances, as shown, the medical delivery device 130 includes an inductive coil 150 that is disposed relative to the outer sheath 134. As the inner rod 132 passes through the outer sheath 134, and the inset ring 140 passes through the inductive coil 150, an electrical current is induced within the inductive coil 150. It will be appreciated that a wire 154 forming the inductive coil 150 extends proximally and forms a first coupling coil 152, thus any induced current flowing through the inductive coil 150 also flows through the first coupling coil 152. A second coupling coil 156 may be disposed about a sheath 154 that may, for example, represent the outer sheath 12 (FIG. 1). In some cases, the second coupling coil 156 may electromagnetically couple with the first coupling coil 152, and thus the electric current induced by the inset ring 140 passing through the inductive coil 150 may be transmitted to a position exterior to the medical delivery device 130. In some instances, the second coupling coil 156 may be secured to the sheath 154. In some cases, the second coupling coil 156 may be temporarily clamped to the sheath 154 when needed.

The materials that can be used for the various components of the medical devices and/or system 10 disclosed herein may include those commonly associated with medical devices. However, this is not intended to limit the devices and methods described herein, as the discussion may be applied to other components of the medical devices and/or systems 10 disclosed herein including the various shafts, liners, components described relative thereto.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel- copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MM) compatibility is imparted into the medical device 10. For example, the medical device 10 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MM machine can image. Some materials that exhibit these characteristics include, for example, tungsten, cobalt- chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system for an implantable medical device, comprising:

an outer shaft defining an outer shaft lumen;

an inner shaft translatable within the outer shaft lumen;

the inner shaft defining a lumen extending through the inner shaft;

an actuation mechanism extending through the lumen, the actuation mechanism including a coupler, a force translation rod that extends proximally from the coupler and a plurality of push pull rods that extend distally from the coupler and that releasably couple to the implantable medical device;

the force translation rod including a transition in electromagnetic permeability and wherein the force translation rod is formed of a material having a low electromagnetic permeability material and the translation in electromagnetic permeability comprises an inset band of a high electromagnetic permeability material; and an inductive coil disposed relative to the force translation rod, relative to the inner shaft, and positioned to detect a change in inductance resulting from the transition in electromagnetic permeability passing through the inductive coil, wherein the inductive coil is electrically coupled with a first coupling coil that is disposed relative to the inner shaft, at or near a proximal region of the delivery system, and is magnetically coupled with a second coupling coil that is disposed about the outer shaft.

2. The delivery system of claim 1, wherein the transition in electromagnetic permeability is positioned a distance from the coupler such that a detected change in inductance indicates a relative position of the coupler relative to the inductive coil.

3. The delivery system of claim 1, wherein a portion of the force translation rod distal of the transition in electromagnetic permeability is formed of a material having a first electromagnetic permeability and a portion of the force translation rod proximal of the transition in electromagnetic permeability is formed of a material having a second electromagnetic permeability different from the first electromagnetic permeability.

4. The delivery system of claim 1, wherein the force translation rod comprises Nitinol as a low electromagnetic permeability material and stainless steel as a high electromagnetic permeability material.

5. The delivery system of claim 1, wherein the inductive coil has a constant windings pitch.

6. The delivery system of claim 1, wherein the inductive coil has a non-constant windings pitch in order to provide increased sensitivity to small movements of the transition in electromagnetic permeability relative to the inductive coil.

7. A delivery catheter for delivering an implantable medical device, comprising:

an outer shaft;

an inner shaft slidingly disposed within the outer shaft and defining a lumen extending through the inner shaft, the implantable medical device securable relative to the inner shaft;

a force translation rod extending through the lumen of the inner shaft, the force translation rod including a first section formed of a material having a low electromagnetic permeability and a second section formed of a material having a high electromagnetic permeability such that a transition in electromagnetic permeability exists between the first section and the second section; and an inductive coil disposed relative to the force translation rod, disposed relative to the inner shaft, and positioned to detect a change in inductance resulting from the transition in electromagnetic permeability passing through the inductive coil, wherein the inductive coil is electrically coupled with a first coupling coil that is disposed relative to the inner shaft, at or near a proximal region of the delivery catheter, and is magnetically coupled with a second coupling coil that is disposed about the outer shaft.

8. The delivery catheter of claim 7, wherein the transition in electromagnetic permeability is positioned a known distance from where the implantable medical device is secured relative to the inner shaft.

9. The delivery catheter of claim 7, wherein the force translation rod extends distally to a coupler, and a plurality of push pull rods extend distally from the coupler, and the transition in electromagnetic permeability is positioned a known distance from the coupler.

10. The delivery catheter of claim 7, wherein the inductive coil has a constant windings pitch.

11. A delivery system for an implantable medical device, comprising:

Ari an inner shaft defining an inner shaft lumen;

an actuation mechanism extending through the inner shaft lumen, the actuation mechanism including a coupler, a force translation rod that extends proximally from the coupler and a plurality of push pull rods that extend distally from the coupler and that releasably couple to the implantable medical device;

the force translation rod including a transition in electromagnetic permeability; and an inductive coil disposed relative to the force translation rod and positioned to detect a change in inductance resulting from the transition in electromagnetic permeability passing through the inductive coil, wherein the inductive coil is electrically coupled with a first coupling coil that is disposed relative to the inner shaft, at or near a proximal region of the delivery system, and is magnetically coupled with a second coupling coil that is disposed about an outer shaft.

12. The delivery system of claim 11, wherein the transition in electromagnetic permeability is positioned a distance from the coupler such that a detected change in inductance indicates a relative position of the coupler relative to the inductive coil.

13. The delivery system of claim 11, wherein a portion of the force translation rod distal of the transition in electromagnetic permeability is formed of a material having a first electromagnetic permeability and a portion of the force translation rod proximal of the transition in electromagnetic permeability is formed of a material having an electromagnetic permeability different from the first electromagnetic permeability.

* * * * *